US00PP20008P2

(12) United States Plant Patent
Silva

(10) Patent No.: US PP20,008 P2
(45) Date of Patent: May 19, 2009

(54) ***CORNUS* PLANT NAMED 'TRI-SPLENDOR'**

(50) Latin Name: *Cornus kousa ssp. chinensis*
Varietal Denomination: Tri-Splendor

(76) Inventor: Crispin Silva, 31997 S. One Way Mololla, Molalla, OR (US) 97036

( * ) Notice: Subject to any disclaimer, the term of this patent is extended or adjusted under 35 U.S.C. 154(b) by 0 days.

(21) Appl. No.: 12/074,117

(22) Filed: Mar. 3, 2008

(51) Int. Cl.
*A01H 5/00* (2006.01)

(52) U.S. Cl. ..... Plt./220

(58) Field of Classification Search ..... Plt./220
See application file for complete search history.

*Primary Examiner*—Kent L Bell

(57) ABSTRACT

A new cultivar of *Cornus* plant named 'TRI-SPLENDOR' that is characterized by variegated spring foliage and variegated flowers. The foliage color changes to solid green in the summer and then to reddish-purple in the fall. In combination these traits set 'TRI-SPLENDOR' apart from all other existing varieties of *Cornus* known to the inventor.

4 Drawing Sheets

Genus: *Cornus.*
Species: *kousa ssp. chinensis.*
Denomination: TRI-SPLENDOR.

BACKGROUND OF THE INVENTION

The present invention relates to a new and distinct cultivar of *Cornus* or Chinese dogwood that is grown for use as a landscape tree. It is known botanically as *Cornus kousa ssp. chinensis* and will be referred to hereinafter by the cultivar name 'TRI-SPLENDOR'.

'TRI-SPLENDOR' arose and was selected by the inventor at the inventor's nursery in Molalla, Oreg., as a chance seedling in a crop of *Cornus kousa ssp. chinensis* (species, unpatented) in 2000.

The new *Cornus* variety 'TRI-SPLENDOR' is an upright tree characterized by variegated foliage which vary in the spring from lime green to yellow to cream and variegated green and cream colored flowers.

The closest known comparison plant known to the breeder is the parent plant which has solid green leaves and cream colored flowers. The foliage and flowers of 'TRI-SPLENDOR' are variegated and change through the year. In the spring there are three distinct colors on the leaves: the margins are yellow by the base, creamy white towards the apex and the centers are green. By the end of the summer the leaves have turned all green, then in the fall become a pink-reddish hue before dropping. The late spring blooming flowers have bracts which are variegated cream and green. Other cultivars that are close in being variegated *Cornus kousa ssp. chinensis* are Samaritan 'Samzam' and 'Snow Flake'. 'TRI-SPLENDOR' has broader leaves and more pronounced variegation than 'Samzam' and variegated bracts instead of the solid white flowers of 'Snow Flake'.

Asexual reproduction of the new cultivar was first accomplished by the inventor in 2002 in a cultivated area of Molalla, Oreg. The method of asexual propagation used was side veneer grafting in which the scion is inserted into a slit on the side of the rootstock. Since that time the characteristics of the new cultivar have been determined stable and are reproduced true to type in successive generations of asexual propagation.

SUMMARY OF THE INVENTION

The following traits have been repeatedly observed and represent the characteristics of the new *Cornus* cultivar 'TRI-SPLENDOR'. These traits in combination distinguish 'TRI-SPLENDOR' from all other varieties of *Cornus* known to the inventor. 'TRI-SPLENDOR' has not been tested under all possible conditions and phenotypic differences may be observed with variations in environmental, climatic and cultural conditions, without however any change in genotype.

1. *Cornus* 'TRI-SPLENDOR' exhibits vigorous upright growth.
2. *Cornus* 'TRI-SPLENDOR' foliage are variegated green, yellow and cream in the spring.
3. *Cornus* 'TRI-SPLENDOR' foliage is bright green in the summer.
4. *Cornus* 'TRI-SPLENDOR' foliage is reddish-purple in the fall.
5. *Cornus* 'TRI-SPLENDOR' blooms in late spring.
6. The flowers of *Cornus* 'TRI-SPLENDOR' are variegated green and cream.
7. *Cornus* 'TRI-SPLENDOR' is hardy to USDA Hardiness Zone 6.

BRIEF DESCRIPTION OF THE DRAWINGS

The accompanying color drawings illustrate the overall appearance of the new *Cornus* variety 'TRI-SPLENDOR' showing colors as true as it is reasonably possible to obtain in colored reproductions of this type. The specimen in the drawings is a 5 year old tree grown out of doors in Mollala, Oreg. Colors in the drawings may differ from the color values cited in the detailed botanical description, which accurately describe the actual colors of the new variety 'TRI-SPLENDOR'.

Figure 1:
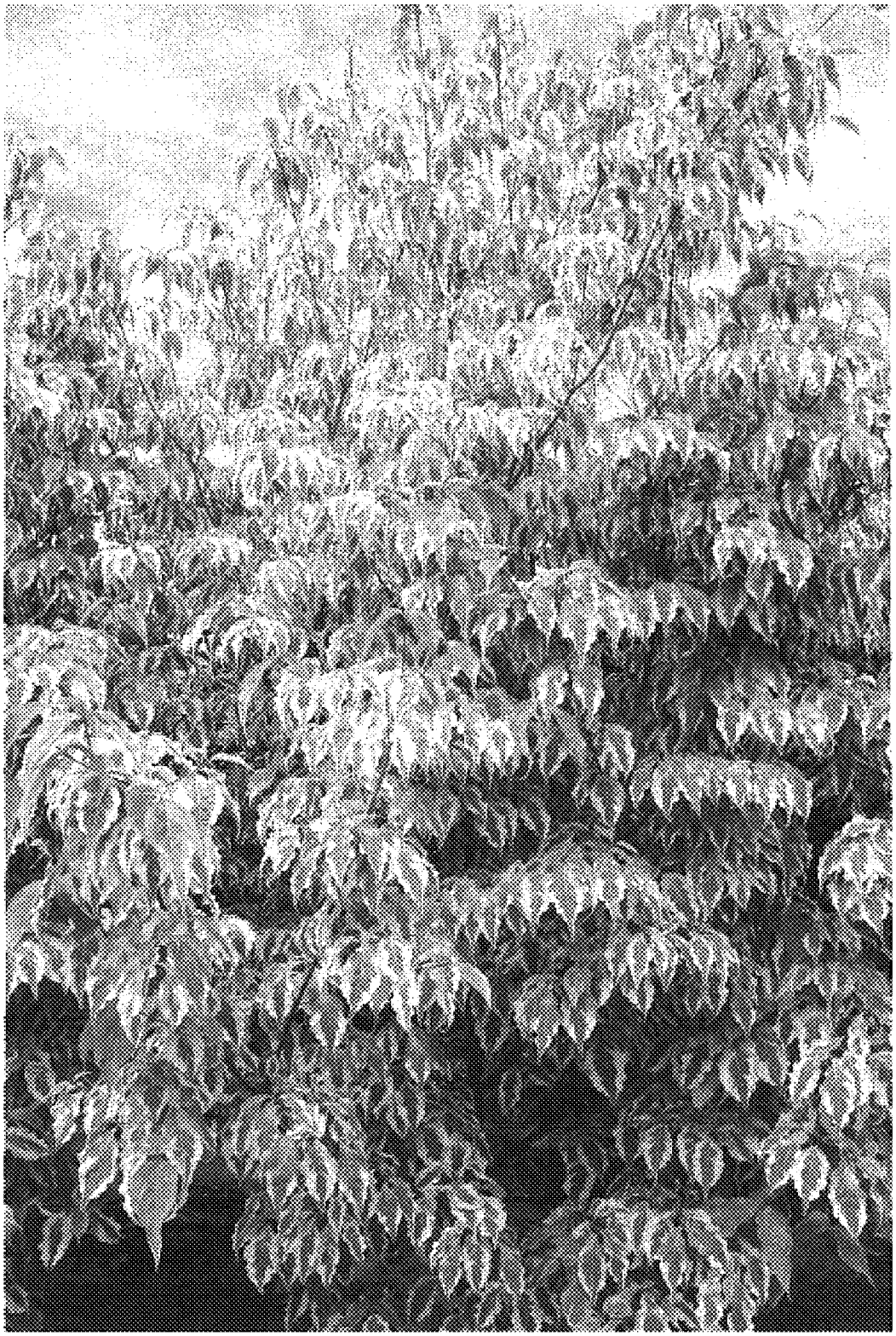
FIG. 1 shows the variegated spring foliage of 'TRI-SPLENDOR'.
Figure 2:
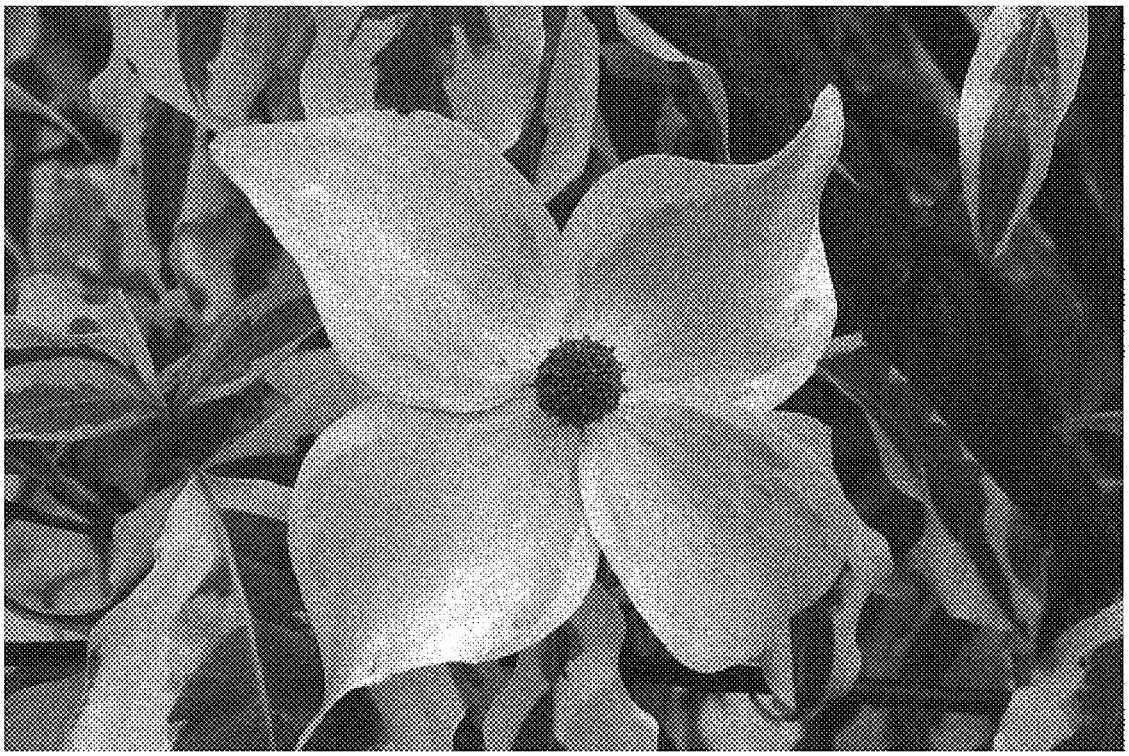
FIG. 2 shows a close-up view of the variegated flower of 'TRI-SPLENDOR'.
Figure 3:
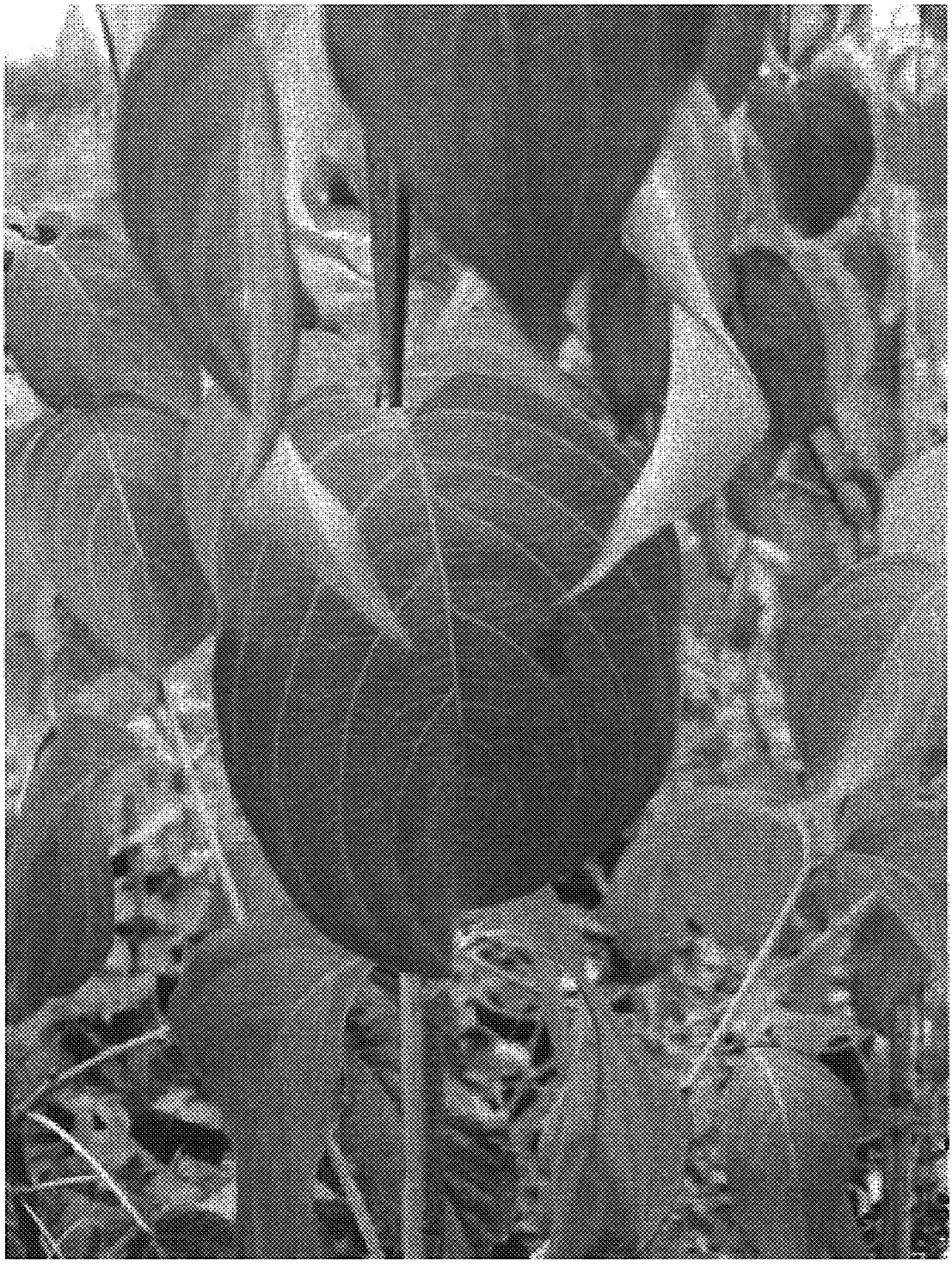
FIG. 3 shows the fall foliage color of 'TRI-SPLENDOR'.
Figure 4:
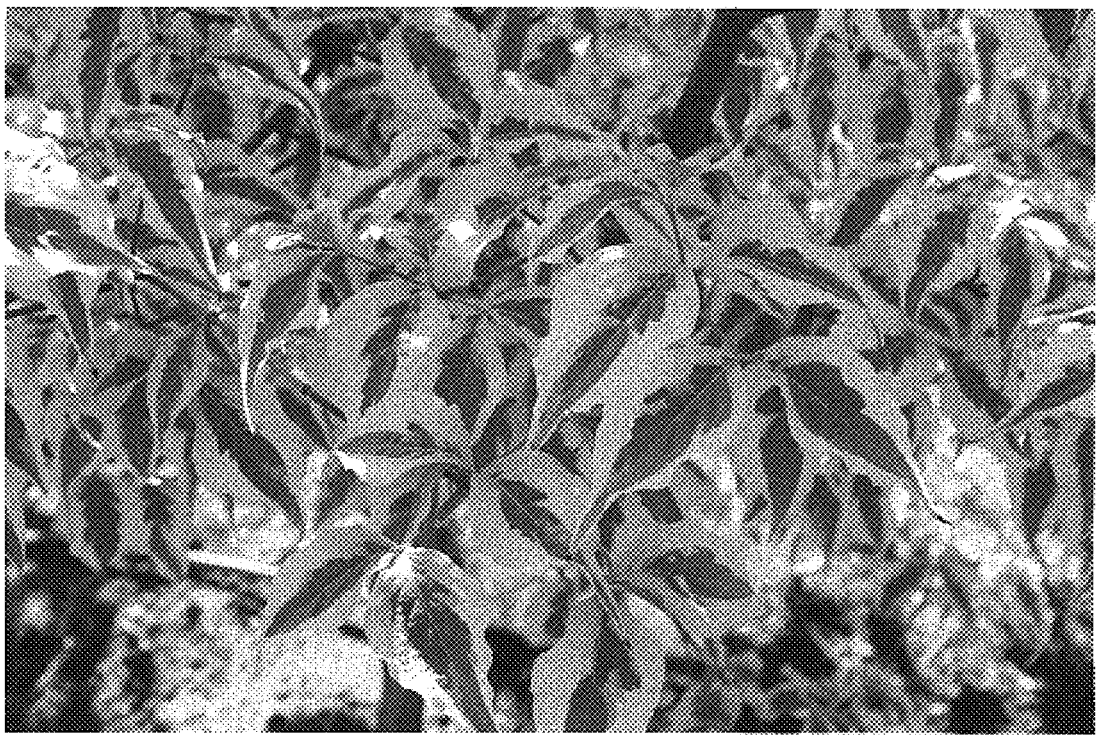
FIG. 4 shows the spring foliage color of 'TRI-SPLENDOR'.

All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'TRI-SPLENDOR'. Data was collected from a 5 year old plant grown in out of doors in Mollala, Oreg. The color determinations are in accordance with the 1966 edition of The Royal Horticultural Society Colour Chart of The Royal Horticultural Society, London, England, except where general color terms of ordinary dictionary significance are used. No chemicals were used to treat the plants.

Botanical classification: *Cornus.*
Species: *kousa ssp. chinensis.*
Common name: Chinese dogwood.
Commercial classification: Deciduous flowering tree.
Use: Landscape plant.
Parentage: *Cornus kousa ssp. chinensis.*
Plant description:

*Plant habit.*—Upright.
*Plant dimensions* (*1 year*).—1 m in height and 1 cm in diameter.
*Plant dimensions* (*5 years*).—3.3 m in height and 2 m in width.
*Plant hardiness.*—USDA Zone 5–9.
*Type.*—Deciduous flowering tree.
*Propagation.*—Grafting, budding, or with semi-hardwood cuttings.
*Growth rate.*—Vigorous— faster than other cultivars in the species.
*Cultural requirements.*—Moist soil with good drainage.
*Diseases and pests.*—None known to the inventor.

Branching habit: Ascending.
Crotch angle: 35–40 degrees away from the vertical.
Stem:

*Color.*—197C.
*Main trunk at* 10 cm height.—16.5 cm.
*Surface.*—Pubescent.
*Lenticels.*—Sparse, approximately 3 cm–5 cm apart.
*Lenticel size on 3 year old branch.*—1 mm in length by 0.5 mm in width.
*Lenticel color.*—197C or darker.

Foliage:

*Arrangement.*—Opposite.
*Leaves.*—Division: Simple. Shape: Ovate to elliptic. Dimensions: 10 cm to 14.5 cm in length and 4.5 cm to 7.5 cm in width. Tip: Acuminate. Base: Acute. Venation pattern: Pinnate. Vein color: As adjacent lamina. Margin: Undulate. Surface (both surfaces): Slightly rough due to the presence of many fine whitish hairs. Immature leaf color (adaxial): Outer margin 151B; leaf center 144A. Immature leaf color (abaxial): Outer margin 151A; leaf center 146B. Mature leaf color (adaxial): Outer margin 1D; leaf center 137B. Mature leaf color (abaxial): Outer margin 2D; leaf center 138C. Fall leaf color: 51A and 51B and 145B seen on individual leaves. Leaf attachment: Petiolate. Petiole dimensions: 10.0 mm in length and 1.5 mm in diameter. Petiole surface: Rough. Petiole color: Immature 144C; Mature 145B.
*Inflorescence.*—Form: Capitate cymes. Quantity of flowers per inflorescence: 20–40. Time and duration of flowering: Late May-June; bracts persisting up to 1 month. Floral bracts: Present. Fused or unfused: Unfused. Shape: Elliptic to broadly elliptic. Number: 4. Color (adaxial surface): Outer margin 155D; center 134C. Color (abaxial surface): Outer margin 155D; center 145C. Surface: Glabrous. Dimensions: 5.75 cm in length and 3.8 cm in width. Peduncle: 3.5 cm to 7.5 cm in length.
*Reproductive organs.*—Style: Cylindrical. Stamen number: 4. Stamen dimensions: Approximately 3 mm in length and 0.3 mm in width. Stamen color: 155C. Anther dimensions: Approximately 0.5 mm in length and 0.75 mm in width. Anther color: 162B.
*Seed.*—None observed to date.

It is claimed:

1. A new and distinct cultivar of *Cornus* plant named 'TRI-SPLENDOR' as described and illustrated herein.

* * * * *